US009295834B2

(12) United States Patent
Wulfman et al.

(10) Patent No.: US 9,295,834 B2
(45) Date of Patent: *Mar. 29, 2016

(54) COIL ELECTRODE FITTING

(71) Applicant: Cardiac Pacemakers, Inc., St. Paul, MN (US)

(72) Inventors: David R. Wulfman, Minneapolis, MN (US); Michael A. Felling, Osceola, WI (US)

(73) Assignee: Cardiac Pacemakers, Inc., St. Paul, MN (US)

(*) Notice: Subject to any disclaimer, the term of this patent is extended or adjusted under 35 U.S.C. 154(b) by 80 days.

This patent is subject to a terminal disclaimer.

(21) Appl. No.: 14/154,413

(22) Filed: Jan. 14, 2014

(65) Prior Publication Data

US 2014/0200641 A1     Jul. 17, 2014

Related U.S. Application Data

(60) Provisional application No. 61/752,771, filed on Jan. 15, 2013.

(51) Int. Cl.
*A61N 1/05* (2006.01)
*A61N 1/375* (2006.01)

(52) U.S. Cl.
CPC .............. *A61N 1/0563* (2013.01); *A61N 1/375* (2013.01)

(58) Field of Classification Search
CPC ................................ A61N 1/0563; A61N 1/056
See application file for complete search history.

(56) References Cited

U.S. PATENT DOCUMENTS

| 5,014,720 | A | | 5/1991 | Barcel et al. |
| 5,522,872 | A | | 6/1996 | Hoff |
| 6,141,593 | A | * | 10/2000 | Patag ............................ 607/122 |
| 6,456,888 | B1 | * | 9/2002 | Skinner et al. ................ 607/116 |
| 9,037,260 | B2 | | 5/2015 | Wulfman et al. |
| 2005/0228469 | A1 | * | 10/2005 | Zarembo et al. .............. 607/122 |
| 2009/0281607 | A1 | * | 11/2009 | Arnholt .......................... 607/122 |
| 2010/0249892 | A1 | * | 9/2010 | Bulkes et al. ................. 607/116 |
| 2010/0305670 | A1 | | 12/2010 | Hall et al. |
| 2011/0079423 | A1 | | 4/2011 | Zhao et al. |
| 2011/0245887 | A1 | | 10/2011 | Klardie et al. |
| 2011/0282420 | A1 | | 11/2011 | Seifert et al. |

FOREIGN PATENT DOCUMENTS

WO      2014113361 A1     7/2014

OTHER PUBLICATIONS

International Search Report and Written Opinion issued in PCT/US2014/011406, mailed May 6, 2014, 8 pages.
(Continued)

*Primary Examiner* — George Evanisko
(74) *Attorney, Agent, or Firm* — Faegre Baker Daniels LLP

(57) ABSTRACT

Various embodiments concern an implantable lead having a coil electrode, configured to deliver defibrillation therapy, made from filars wound in a helical pattern to have a pitch. An end of the coil electrode can be received within a lumen of a tubular fitting, the lumen having threading that corresponds to the pitch of the filars. A wall of a polymer sleeve extending over the coil electrode can be pinched between the threading of the lumen and the filars to mechanically couple the polymer sleeve to the tubular fitting. The polymer sleeve can be porous to permit delivery of the defibrillation through the wall to tissue. Reception of the polymer sleeve within the lumen of the tubular fitting can allow the entire coil electrode to be within the polymer sleeve to prevent direct contact between tissue and the coil electrode.

20 Claims, 5 Drawing Sheets

(56) References Cited

OTHER PUBLICATIONS

International Search Report and Written Opinion issued in PCT/US2014/011479, mailed Apr. 10, 2014, 9 pages.

International Preliminary Report on Patentability issued in PCT/US2014/011406, mailed Jul. 30, 2015, 5 pages.

International Preliminary Report on Patentability issued in PCT/US2014/011479, mailed Jul. 30, 2015, 6 pages.

* cited by examiner

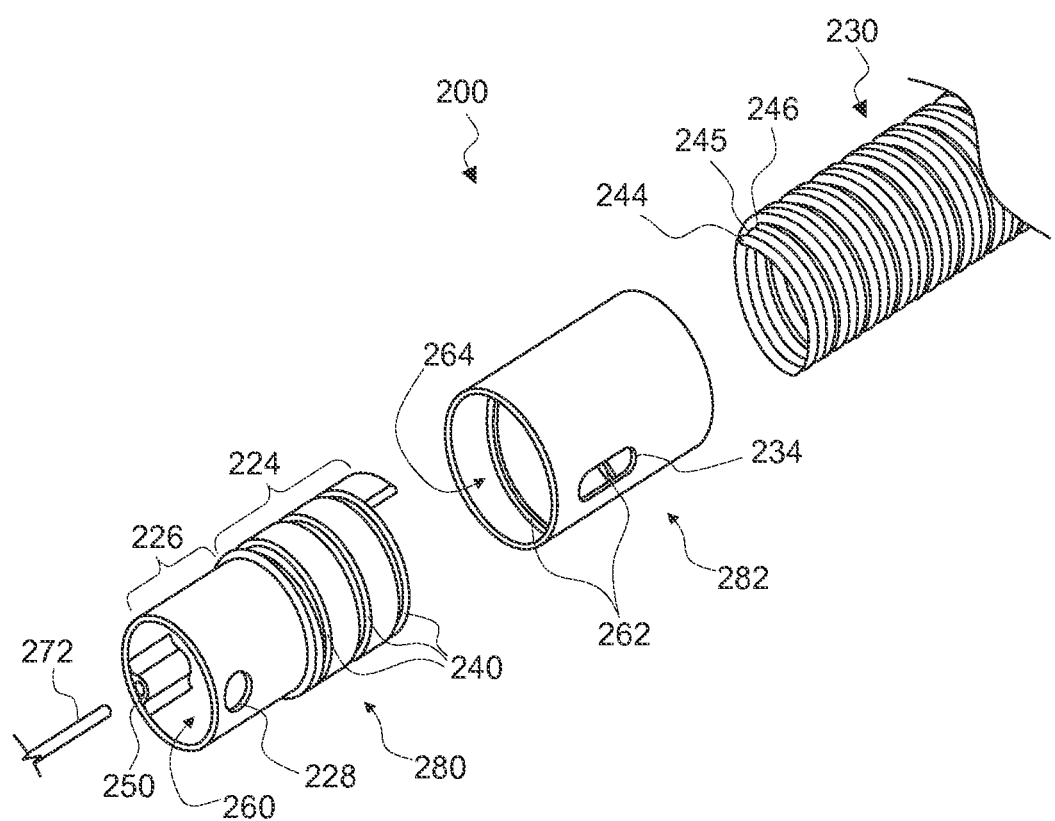

COIL ELECTRODE FITTING

CROSS-REFERENCE TO RELATED APPLICATION

This application claims priority to U.S. Provisional Application 61/752,771, filed Jan. 15, 2013, which is herein incorporated by reference in its entirety.

TECHNICAL FIELD

The present disclosure relates generally to implantable leads. More specifically, the present disclosure relates to fittings for a coil electrode of an implantable lead.

BACKGROUND

When functioning properly, the human heart maintains its own intrinsic rhythm and is capable of pumping adequate blood throughout the body's circulatory system. However, some individuals have irregular cardiac rhythms, referred to as fibrillation or arrhythmias, which can result in improper cardiac rhythms. One manner of treating improper cardiac rhythms include the use of a pulse generator (PG) such as a pacemaker, an implantable cardioverter defibrillator (ICD), or a cardiac resynchronization (CRT) device. Such devices are typically coupled to one or more implantable leads having one or more elements that can be used to deliver electrical energy to the heart. Implantable leads can additionally or alternatively be used to stimulate other tissues of the body, such as nervous and/or musculature systems.

SUMMARY

Example 1 concerns an implantable lead comprising: a lead body having a proximal end and a distal end; a conductor extending within the lead body; a coil electrode having a proximal end, a distal end, and one or more filars, the coil electrode extending along a portion of the distal end of the lead body and configured to deliver defibrillation therapy to tissue, the one or more filars wound in a helical pattern to have a pitch; and a tubular fitting having a lumen, the tubular fitting formed from an electrically conductive metal, at least a portion of the lumen having threading that corresponds to the pitch of the one or more filars, the tubular fitting electrically connecting the conductor to the coil electrode, wherein one of the proximal end or the distal end of the coil electrode is within the lumen of the tubular fitting and the coil electrode is mechanically connected to the tubular fitting by interaction between the threading of the lumen and the one or more filars.

In example 2, the implantable lead of example 1, further comprising a polymer sleeve having a wall, the polymer sleeve extending over the coil electrode, the wall of the polymer sleeve configured to allow the delivery of the defibrillation therapy through the wall.

In example 3, the implantable lead of example 2, wherein the polymer sleeve extends into the lumen of the tubular fitting, the wall of the polymer sleeve pinched between the threading of the lumen and the one or more filars to mechanically couple the polymer sleeve to the tubular fitting.

In example 4, the implantable lead of either of examples 2 or 3, wherein the polymer sleeve is made of expanded polytetrafluoroethylene (ePTFE).

In example 5, the implantable lead of any preceding example, wherein the one or more filars comprises a plurality of filars arranged in a grouping of adjacent filars that spirals in the helical pattern, and a space exists between each turn of the grouping.

In example 6, the implantable lead of example 5, wherein the pitch is defined by the space between each turn of the grouping.

In example 7, the implantable lead of any preceding example, wherein the fitting comprises: an inner fitting axially aligned with the coil electrode, at least a portion of the inner fitting comprising external threading; and an outer tubular fitting, the outer tubular fitting defining the lumen, the inner fitting at least partially received within the lumen, both of the external threading and the one or more filars threadedly engaged with the threading of the lumen.

In example 8, the implantable lead of any preceding example, wherein the tubular fitting comprises at least one window that allows welding between the coil electrode and the tubular fitting.

In example 9, the implantable lead of any preceding example, wherein the tubular fitting further comprises a stop within the lumen, the stop limiting the extent to which the proximal end or the distal end of the coil electrode can extend into the lumen.

In example 10, the implantable lead of example 9, wherein the coil electrode is in contact with the stop, and the contact between the coil electrode and the stop provides an electrical connection between the tubular fitting and the coil electrode.

In example 11, the implantable lead of any preceding example, wherein the tubular fitting further comprises a connector within the lumen, and the conductor is mechanically and electrically connected to the connector.

In example 12, the implantable lead of example 11, wherein the conductor is a cable conductor and the connector is a crimp connector that is crimped over the cable conductor.

In example 13, the implantable lead of any preceding example, wherein the tubular fitting defines at least part of an exterior surface of the implantable lead.

Example 14 concerns an implantable lead comprising: a lead body having a proximal end and a distal end; a cable conductor extending within the lead body; a coil electrode having a proximal end, a distal end, and one or more filars, the coil electrode extending along a portion of the distal end of the lead body and configured to deliver defibrillation therapy to tissue, the one or more filars wound in a helical pattern to have a pitch; a proximal tubular fitting having a first lumen, at least a portion of the first lumen having threading that corresponds to the pitch of the one or more filars, the proximal end of the coil electrode within the first lumen and mechanically connected to the proximal tubular fitting by interaction between the threading of the first lumen and the one or more filars; and a distal tubular fitting having a second lumen, at least a portion of the second lumen having threading that corresponds to the pitch of the one or more filars, the distal end of the coil electrode within the second lumen and mechanically connected to the distal tubular fitting by interaction between the threading of the second lumen and the one or more filars.

In example 15, the implantable lead of example 14, wherein either or both of the proximal tubular fitting and the distal tubular fitting electrically connects the conductor to the coil electrode.

In example 16, the implantable lead of either of examples 14 or 15, further comprising a polymer sleeve having a proximal end, a distal end, and a wall, the polymer sleeve extending over the coil electrode, the wall of the polymer sleeve porous to allow the delivery of the defibrillation therapy through the wall.

In example 17, the implantable lead of example 16, wherein the proximal end of the polymer sleeve extends into the first lumen of the proximal tubular fitting and the wall is pinched between the threading of the first lumen and the one or more filars to mechanically couple the polymer sleeve to the proximal tubular fitting; and the distal end of the polymer sleeve extends into the second lumen of the distal tubular fitting and the wall is pinched between the threading of the second lumen and the one or more filars to mechanically couple the polymer sleeve to the distal tubular fitting.

In example 18, the implantable lead of any of examples 14-17, wherein the one or more filars comprises a plurality of filars arranged in a grouping of adjacent filars that spirals in the helical pattern, and a space exists between each turn of the grouping.

In example 19, the implantable lead of example 18, wherein the threading of each of the proximal tubular connector and the distal tubular connector is dimensioned such that each thread projects into the space between each turn of the grouping.

Example 20 concerns an implantable lead comprising: a lead body having a proximal end and a distal end; a conductor extending within the lead body from the proximal end to the distal end; a coil electrode having a proximal end, a distal end, and one or more filars, the coil electrode extending along a portion of the distal end of the lead body and configured to deliver defibrillation therapy to tissue; a tubular fitting having an exterior surface, a lumen, and a window providing access to the lumen from the exterior surface, the tubular fitting formed from an electrically conductive metal; and a weld joint between the coil electrode and the tubular fitting, wherein one of the proximal end or the distal end of the coil electrode is within the lumen of the tubular fitting and the weld joint is proximate the window.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIG. 4 is a perspective view of a coupling assembly.

Figure 1:
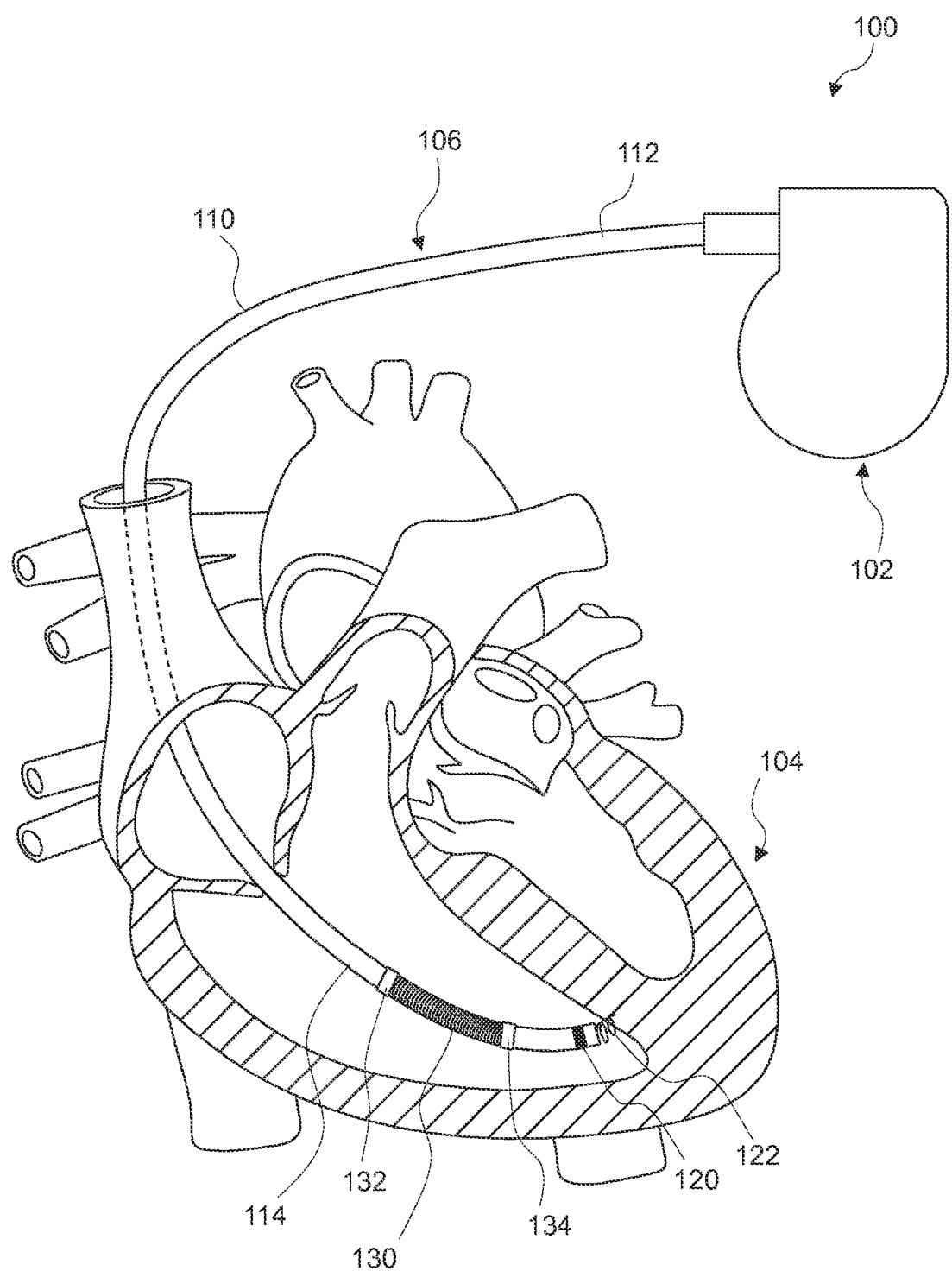
FIG. 1 is a schematic view of a cardiac rhythm management system including a pulse generator and an implantable lead.

While the disclosure is amenable to various modifications and alternative forms, specific embodiments have been shown by way of example in the drawings and are described in detail below. The intention, however, is not to limit the disclosure to the particular embodiments described herein. On the contrary, the disclosure is intended to cover all modifications, equivalents, and alternatives falling within the scope of the disclosure as defined by the appended claims.

DETAILED DESCRIPTION

FIG. 1 illustrates a schematic view of a cardiac rhythm management (CRM) system 100. The CRM system can include a pulse generator 102 for delivering electrical stimulation to the heart 104. The pulse generator 102 can be implanted subcutaneously within an implantation location or pocket in the patient's chest or abdomen. The pulse generator 102 can be connected to an implantable lead 106. The implantable lead 106 can conduct electrical signals between the pulse generator 102 and the heart 104 or other tissue. The implantable lead 106 can include a lead body 110, a proximal end 112, and a distal end 114. The proximal end 112 of the implantable lead 106 can mechanically and electrically connect with the pulse generator 102. In various embodiments, the implantable lead 106 can enter the vascular system through a vascular entry site formed in the wall of the left subclavian vein or other location. The implantable lead 106 can extend through the left brachiocephalic vein and the superior vena cava such that the distal end 114 of the implantable lead 106 can be implanted in or along any of the right atrium, left atrium, right ventricle, left ventricle, or other location.

The distal end 114 of the implantable lead 106 can include one or more electrodes for sensing bioelectrical signals and/or delivering electrical energy to the heart 104. For example, the distal end 114 of the implantable lead 106 can include a ring electrode 120. The distal end 114 of the implantable lead 106 can include a fixation element 122 which, in addition to anchoring the distal end 114 to tissue, can be configured to sense bioelectrical signals and/or deliver electrical energy. The distal end 114 can include a coil electrode 130, which is further discussed herein. The coil electrode 130 can be configured to sense bioelectrical signals and/or deliver electrical energy. While one coil electrode 130 is illustrated in FIG. 1, various embodiments of the implantable lead 106 may include a plurality of coil electrodes, such as two or more coil electrodes.

The coil electrode 130 can extend along a portion of the distal end 114 of the lead body 110. In some embodiments, the coil electrode 130 can be exposed, as shown in FIG. 1. In some embodiments, the coil electrode 130 can be partially or fully covered by a polymer sleeve, as further discussed herein. A conductor can extend within the lead body 110 to electrically connect the pulse generator 102 and the coil electrode 130 to allow the pulse generator 102 to deliver electrical energy to the heart 104 from the coil electrode 130. The coil electrode 130 can be particularly suited for delivering high energy shocks as part of a defibrillation therapy. For example, a high voltage signal that depolarizes a critical mass of cardiac tissue can be delivered through the coil electrode 130 to terminate an arrhythmia and allow a normal sinus rhythm to be reestablished. While use of the coil electrode 130 for delivering a defibrillation therapy to the heart 104 is mainly discussed herein, the coil electrode 130 can be used for delivering other therapies to the heart 104 or other tissues of the body.

The coil electrode 130 can be mechanically and electrically connected to the lead 110 by one or both of tubular fittings 132, 134, as further discussed herein. As shown in FIG. 1, the tubular fitting 132 can be provided on the lead body 110 proximally of the coil electrode 130. As further shown in FIG. 1, the tubular fitting 134 can be provided on the lead body 110 distally of the coil electrode 130. In some embodiments, only one of the tubular fittings 132, 134 may be provided on the lead body 110.

Figure 2:
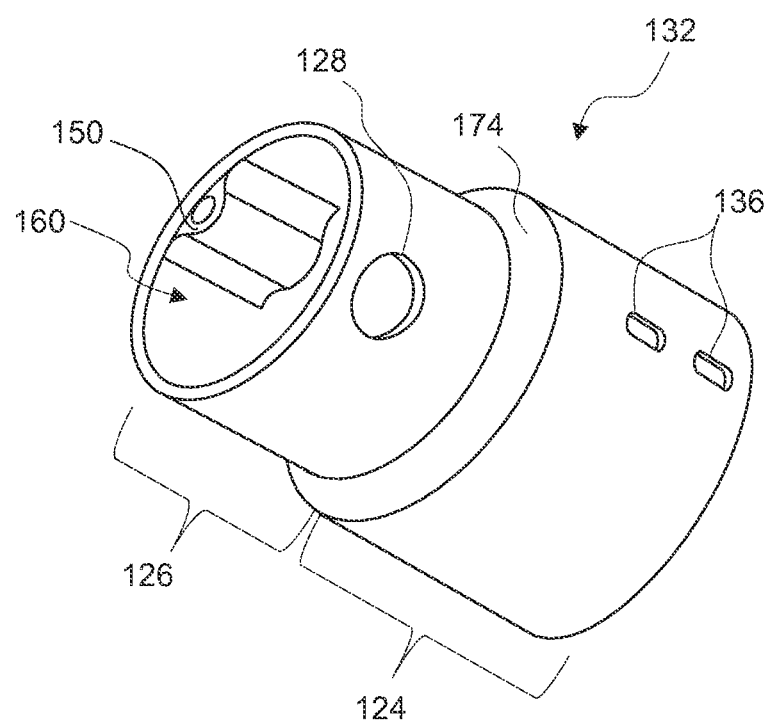
FIG. 2 is a perspective view of a tubular fitting of the implantable lead of FIG. 1.

FIG. 2 is a perspective view of the tubular fitting 132. The tubular fitting 132 may be formed from an electrically conductive material, such as platinum or titanium. The tubular fitting 132 can be formed by one or more of casting, extrusion, stamping, and/or machining processes. The tubular fitting 132 can have a first portion 124 and a second portion 126. The first portion 124 can have an outer diameter that is larger than an outer diameter of the second portion 126. An outer step 174 can be provided between the first portion 124 and the second portion 126 to transition between the different diameters of the first portion 124 and the second portion 126. In some embodiments, an outer circumferential surface of the first portion 124 can define part of an exterior surface of the implantable lead 106 while an outer circumferential surface of the second portion 126 can be insulated within the lead body 110.

A lumen 160 can extend within the tubular fitting 132. The tubular fitting 132 can include a connector 150. As shown in FIG. 2, the connector 150 can be within the lumen 160 along the second portion 126. In some other embodiments, the connector 150 can be located on any of the outer surface of the second portion 126, an inner surface of the lumen 160 along the first portion 124, or other location. In some embodiments, the connector 150 can be formed integrally with the tubular fitting 132. For example, the connector 150 can be formed from the same material as the tubular fitting 132. In some embodiments, the connector 150 can be formed separately from the tubular fitting 132 and then mechanically and electrically connected to the tubular fitting 132.

The connector 150 can mechanically and electrically connect to a conductor, such as a cable conductor. The connector 150 embodiment shown in FIG. 2 can mechanically and electrically connect to a conductor by crimping around the conductor. However, various other types of connectors 150 for mechanically and electrically connecting a conductor and the tubular fitting 132 are contemplated, such as weld joints.

The tubular fitting 132 can include one or more windows 136 along the first portion 124. The one or more windows 136 can allow welding to take place within the lumen 160 of the tubular fitting 132, as further discussed herein. The tubular fitting 132 can include one or more attachment features along the second portion 126. As shown in FIG. 2, the one or more attachment features can comprise a hole 128. Polymer material can be heated to integrate into the hole 128 or other attachment feature to mechanically connect to the tubular fitting 132. The one or more attachment features can additionally or alternatively comprise one or more projections along the second portion 126 which can be encapsulated by the polymer material to support mechanical fixation.

Figure 3A:
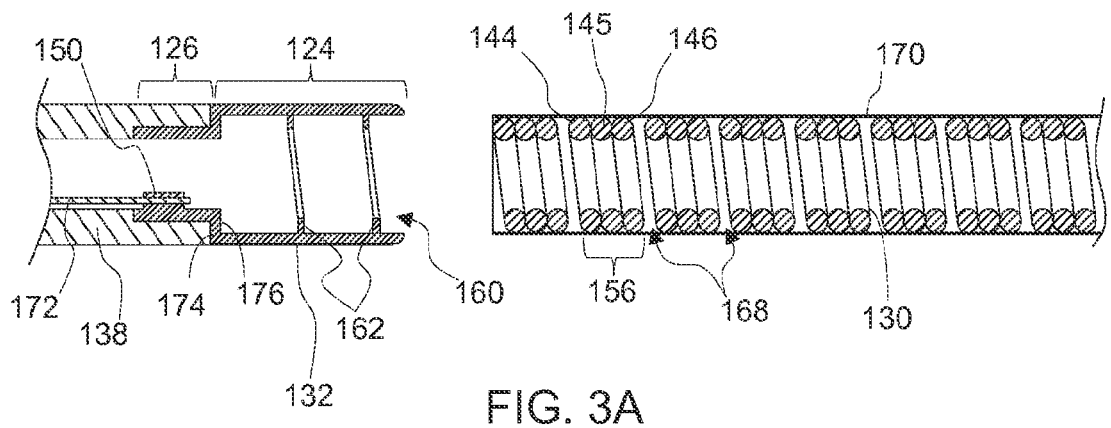
FIGS. 3A-3B are cross-sectional views of the coil electrode and the tubular fitting of FIG. 2.

FIG. 3A shows a cross sectional diagram of the tubular fitting 132. As shown in FIG. 3A, the tubular fitting 132 can be attached to a polymer tube 138. The polymer tube 138 can be formed by an extrusion process and then placed over the second portion 126 of the tubular fitting 132 to engage with the outer step 174. Heat can then be applied to allow polymer material of the polymer tube 138 to integrate into the one or more attachment features 128 (shown in FIG. 2) of the tubular fitting 132. In some embodiments, the polymer tube 138 can be attached to the tubular fitting 132 by an adhesive. In some embodiments, the polymer tube 138 can be formed over the second portion 126 by injection molding.

In some embodiments, the polymer tube 138 can define an exterior surface of the lead body 110. For example, the polymer tube 138 can define an exterior surface of the lead body 110 between the tubular fitting 132 and the proximal end 112 of the implantable lead 106. However, in some embodiments, the polymer tube 138 can be relatively shorter. For example, the polymer tube 138 can be joined to another polymer tube (e.g., an extruded tube) that extends along a majority of the length of the lead body 110. In some embodiments, the polymer tube 138 can have an outer diameter that is about equal to the outer diameter of the first portion 124 of the tubular fitting 132. The polymer tube 138 and the first portion 124 having a similar outer diameter can provide for a relatively smooth exterior surface of the implantable lead 106. It is noted that the larger outer diameter of the first portion 124, relative to the second portion 126, can allow the polymer tube 138 to be placed over the second portion 126 to align with the outer surface of the first portion 124 to define a consistent outer diameter of the implantable lead 106. However, it is noted that in some embodiments the outer diameter of the polymer tube 138 may not be similar to the outer diameter of the first portion 124.

As shown in FIG. 3A, the lumen 160 of the tubular fitting 132 can extend entirely through the tubular fitting 132. In some other embodiments, the lumen 160 may not extend between the first portion 124 and the second portion 126. As shown in FIG. 3A, the inner diameter of the lumen 160 can be relatively larger along the first portion 124 and relatively smaller along the second portion 126.

FIG. 3A further illustrates a coil electrode 130. The coil electrode 130 can extend within a polymer sleeve 170. The polymer sleeve 170 can be formed by expanded polytetrafluoroethylene (ePTFE), for example. The polymer sleeve 170 can be formed in an extrusion process or a molding process. In some embodiments, the wall of the polymer sleeve can be porous such that electrical energy can be delivered from the coil electrode 130 through the wall of the polymer sleeve 170 to tissue outside of the polymer sleeve 170. For example, the porous nature of the polymer sleeve 170 can allow bodily fluid to penetrate the wall of the polymer sleeve 170 to support conduction of electrical energy through the wall. In some embodiments, the wall of the polymer sleeve 170 can be formed by conductive material (e.g., a conductive polymer) to support the passage of electrical energy through the wall of the polymer sleeve 170 to tissue outside of the polymer sleeve 170. The polymer sleeve 170 can prevent tissue ingrowth into the coil electrode 130, wherein the tissue ingrowth may otherwise unintentionally anchor the implantable lead 106 and/or inhibit the delivery of electrical energy from the coil electrode 130.

The inner diameter of the polymer sleeve 170 can be about equal to the outer diameter of the coil electrode 130. In some embodiments, the inner diameter of the polymer sleeve 170 can be larger than the outer diameter of the coil electrode 130, which can allow the coil electrode 130 to move within the polymer sleeve 170. In some embodiments, the inner diameter of the polymer sleeve 170 can be smaller than the outer diameter of the coil electrode 130 in a relaxed state, wherein the coil electrode 130 can be stretched longitudinally to temporarily decrease the outer diameter of the coil electrode 130 to permit the polymer sleeve 170 to be placed over the coil electrode 130.

As shown in FIG. 3A, the lumen 160 can include threading 162. The threading 162 can be formed by one or more spiraling features projecting inward from an inner surface of the lumen 160. The threading 162 can have a pitch. In some embodiments, the pitch of the threading 162 can be measured based on the longitudinal distance along the tubular fitting 132 in which a thread 162 completes a full spiral (e.g., a 360 degree rotation). In some embodiments, the pitch of the threading 162 can be measured based on the longitudinal distance between each thread 162. In some embodiments, the pitch of the threading 162 can be measured based on the number of threads per unit distance (e.g., threads-per-inch).

The coil electrode 130 can be formed by one or more filars. The particular embodiment of the coil electrode 130 shown in FIG. 3A is formed by three filars 144-146, however other embodiments can have a greater or lesser number of filars. The filars 144-146 can be wound in a helical pattern. For example, the coil electrode 130 can be formed by wrapping filars 144-146 around a mandrel in a helical pattern. The filars 144-146 can be thermally treated such that the filars 144-146 are biased to retain the helical pattern. The filars 144-146 can be formed from electrically conductive material, such as platinum or titanium.

As shown in FIG. 3A, the filars 144-146 can form a filar grouping 156. A filar grouping can include a set of separate filars that are adjacent to one another and spiral together in a helical pattern. A space 168 can exist between the filars of adjacent turns of the grouping 156.

The helical pattern of the filars 144-146 can have a pitch. In some embodiments, the pitch can be measured by the distance between each adjacent filar turn (e.g., the longitudinal distance between filar 144 and filar 145). In some embodiments, the pitch can be measured based on the longitudinal distance along the coil electrode 130 in which a particular filar completes one full spiral (e.g., a 360 degree rotation of filar 144 of the grouping 156). In some embodiments, the pitch can be measured based on the longitudinal distance along the coil electrode 130 between adjacent spaces 168. In some embodiments, the pitch can be measured based on the number of filar turns per unit distance (e.g., filars-per-inch).

The helical pattern of the filars 144-146 can form a helical contour pattern along the exterior of the coil electrode 130. The helical contour pattern of the coil electrode 130 can correspond to the threading 162 of the lumen 160 of the tubular fitting 132 such that an end (e.g., a proximal end) of the coil electrode 130 can be rotateably advanced into the lumen 160 to interlock the filars 144-146 and the threading 162 as the end of the coil electrode 130 is received within the lumen 160.

Figure 3B:
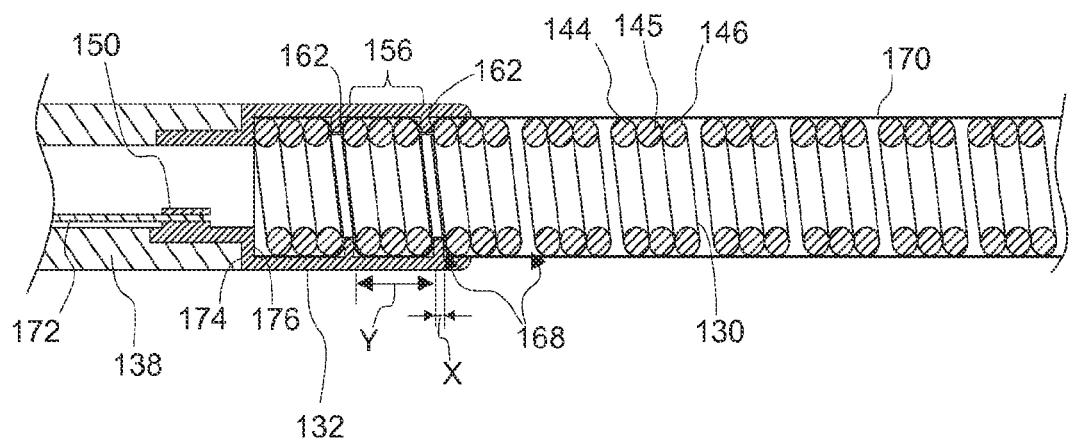

FIG. 3B is a cross sectional diagram showing a proximal end of the coil electrode 130 received within the lumen 160 of the tubular fitting 132. The configuration of FIG. 3B can be the result of inserting the coil electrode 130 into the lumen 160 of the tubular fitting 132 while rotating one or both of the coil electrode 130 and the tubular fitting 132 to interlock the filars 144-146 with the threading 162. As shown in FIG. 3B, the threading 162 can penetrate the spaces 168 between the turns of the grouping 156. Interaction between the threads 162 and the filars 144-146 of the coil electrode 130 can mechanically connect the coil electrode 130 to the tubular fitting 132. The interaction can be facilitated by similarity between the pitch of the filars 144-146 of the coil electrode 130 and the pitch of the threading 162. For example, the pitch of the filars 144-146 can correspond to the pitch of the threading 162. In some cases, the pitch of the filars 144-146 can be about the same or equal to the pitch of the threading 162. The aggregate width of the filars 144-146 formed in the grouping 156 can be about the same as, or slightly smaller than, the longitudinal distance between the threads 162 (e.g., distance "Y"), such that the filars 144-146 formed in the grouping 156 fit between the threads 162. In some cases, the width of each thread 162 is about the same as, or slightly smaller than, the width of the space 168 between each turn of the grouping 156 (e.g., distance "X").

A proximal end of the coil electrode 130 may engage the stop 176 of the tubular fitting 132. The stop 176 can be a narrowing of the lumen 60 of the tubular fitting 132. Engagement between the coil electrode 130 and the stop 176 can electrically connect the coil electrode 130 and the tubular fitting 132. Engagement between the coil electrode 130 and the stop 176 can limit the degree to which the coil electrode 130 can be advanced into the tubular fitting 132.

It is noted that the polymer sleeve 170 can extend over the coil electrode 130 before rotational engagement between the coil electrode 130 and the tubular fitting 132. As shown in FIG. 3B, the wall of the polymer sleeve 170 can be pinched between the coil electrode 130 and an internal surface of the lumen 60. For example, the wall of the polymer sleeve 170 can be pinched between the coil electrode 130 and the threading 162. The pinching of the wall of the polymer sleeve 170 can mechanically fix the polymer sleeve 170 to the tubular fitting 132. In some embodiments, the pinching of the wall of the polymer sleeve 170 can increase the interference between the threads 162 and the filars 144-146 to strengthen the mechanical connection between the coil electrode 130 and the tubular fitting 132. In some embodiments, the polymer sleeve 170 can flex relative to the tubular fitting 132 despite being mechanically attached to the tubular fitting 132. In some embodiments, the coil electrode 130 can move within the polymer sleeve 170.

The tubular fitting 134, shown in FIG. 1 distal of the coil electrode 130, can have a similar configuration as the tubular fitting 132 described and illustrated herein. In some embodiments, the tubular fitting 134 can be structurally identical to the tubular fitting 132. A distal end of the coil electrode 130 can be attached to the tubular fitting 134 in any manner described herein for connecting the proximal end of the coil electrode 130 to the tubular fitting 132. For example, a distal end of the coil electrode 130, covered by the polymer sleeve 170, can be received within a lumen of the tubular fitting 134 and interaction between the filars 144-146 and threads of the lumen can fix the coil electrode 130 and the polymer sleeve 170 to the tubular fitting 134. It is noted that the cable conductor 172 is shown attached to the connector 150 of the tubular fitting 132 in FIGS. 3A-B. However, the cable conductor 172 can additionally or alternatively be coupled to a connector (or other attachment feature) of the tubular fitting 134. In some embodiments, the tubular fitting 134 may not include a connector for attaching to the cable conductor 172.

It is noted that use of the tubular fitting 132 having a lumen 160, and an end of the polymer sleeve 170 extending into the lumen 160, can provide various advantages. For example, a conventional fitting for a coil electrode can have a relatively small outer diameter so as to allow the conventional fitting to be inserted into the lumen of the coil electrode. The fitting, underneath the coil electrode, can then be welded to the defibrillation coil. However, a polymer sleeve extending over the coil electrode may have to leave at least a portion of the coil electrode exposed to allow access to the coil electrode for the welding step (e.g., a window may be cut in the polymer sleeve to allow welding of the coil electrode to the conventional fitting). As such, at least part of the coil electrode can be left exposed. The present disclosure provides embodiments where the entire length of the coil electrode 130 can be covered by the polymer sleeve 170 and the tubular fittings 132, 134. As such, protection from tissue adhesion can be provided by the polymer sleeve 170 along the entire coil electrode 130.

Returning to FIG. 2, the one or more windows 136 can be used to weld the coil electrode 130, received within the lumen 160, to the tubular fitting 132. In some embodiments, a part of the polymer sleeve 170 can be removed through the window 136 to expose a portion of the coil electrode 130 within the window 136. A welding tool can then weld within the window 136 to electrically and mechanically connect the coil electrode 130 to the tubular fitting 132. While engagement between the filars 144-146 of the coil electrode 130 and the threading 162 of the tubular fitting 132 can form a mechanical connection, a weld as described above can prevent the coil electrode 130 from unscrewing from the lumen 160 of the tubular fitting 132. In some embodiments, threading 162 may not be provided within the lumen 160 of the tubular fitting 132. In such embodiments, a proximal end of the coil electrode 130 can be received within the lumen 160 of the tubular fitting 132 and the coil electrode 130 can be mechanically and electrically attached to the tubular fitting 132 by welding the coil electrode 130 to the tubular fitting 132 through one or more of the windows 136.

In some embodiments, the polymer sleeve 170 can be shorter than the coil electrode 130, such that some portion of either or both of the proximal end and the distal end of the coil electrode 130 may not be covered by the polymer sleeve 170. In such embodiments, the proximal and/or distal ends of the coil electrode 130 can directly contact the interior surfaces of the tubular fittings 132, 134, respectively. However, the polymer sleeve 170 can be long enough to extend between the tubular fittings 132, 134 such that the polymer sleeve 170 is received within one or both of the tubular fittings 132, 134 and no part of the coil electrode 130 is exposed on the exterior of the implantable lead 106. For example, the polymer sleeve 170 can be pinched between the exterior of the coil electrode 130 and the interior surface of the tubular fitting 132 even though the polymer sleeve 170 does not extend along the entire length of the coil electrode 130. It is noted that some embodiments may not include the polymer sleeve 170. As such, the coil electrode 130 may be exposed along the exterior of the implantable lead 106. In such cases, the filars 144-146 of the coil electrode 130 can directly engage the interior surface of the tubular fitting 124.

The one or more conductors can electrically connect the pulse generator 102 to the ring electrode 120 and/or the fixation element 122.

It is noted that various components can extend within the lead body 110 through one or both of the tubular fittings 132, 134. For example, one or more passageways can extend through the polymer tube 138, the tubular fitting 132, and the coil electrode 130 (e.g., along the lumen 160 of the tubular fitting 132) and one or more elongated components can extend within the one or more passageways. In some embodiments, an elongated polymer member (not illustrated) having one or more lumens containing one or more conductors can extend from the proximal end 112 to the distal end 114 of the implantable lead 106. The elongated polymer member can extend within the lumen 160 of the tubular fitting 132 and within the coil electrode 130. The elongated polymer member can be, for example, a tri-lumen tube containing one or more cable conductors and/or coil conductors. The one or more conductors within the elongated polymer member can electrically connect to the ring electrode 120 and/or the fixation element 122, for example. In some cases, the cable conductor 172 can extend within a lumen of the elongated polymer member proximally of the tubular fitting 132, extend outside of the elongated polymer member to mechanically and electrically connect with the tubular fitting 132, and reenter the lumen of the elongated polymer member distally of the tubular fitting 132. The cable conductor 172 can again extend outside of the elongated polymer member at a location proximal of the tubular fitting 134 but distal of the tubular fitting 132 to mechanically and electrically connect with the tubular fitting 134.

Figure 5:
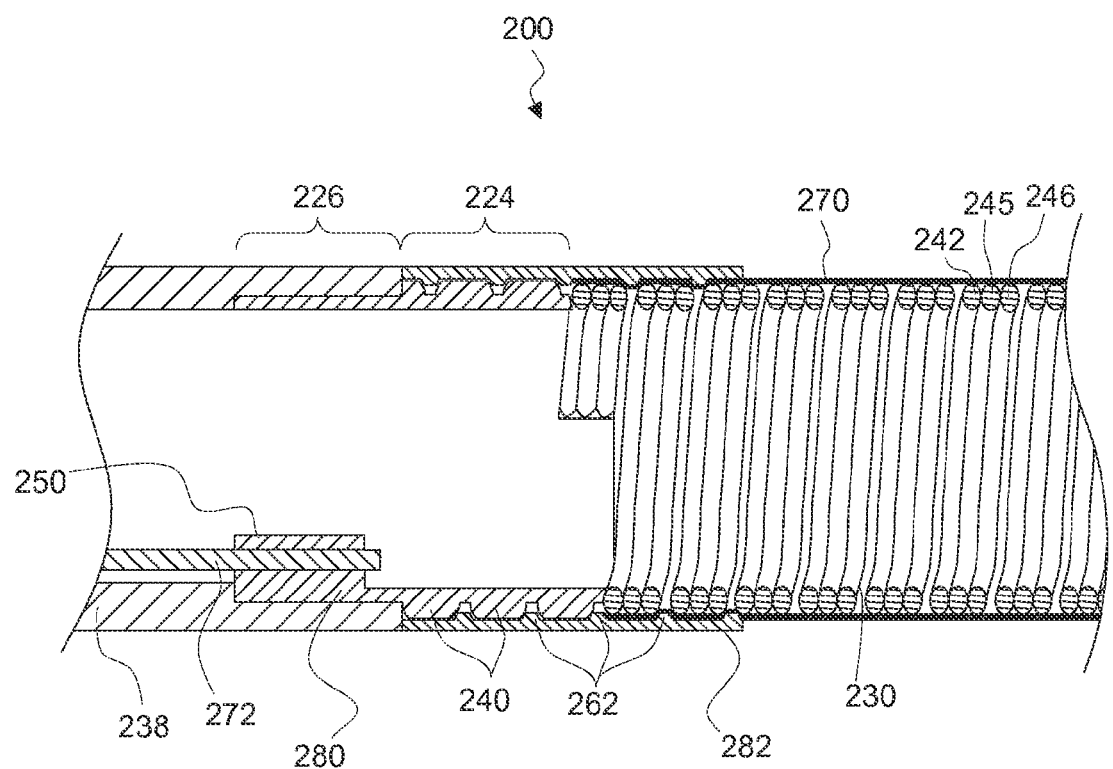
FIG. 5 is a cross-sectional view of the coupling assembly.

While FIGS. 2-3B concern a unitary body tubular fitting 132, some other embodiments can concern a fitting formed from multiple parts. FIGS. 4-5 illustrate a coupling 200 that can mechanically and electrically connect a cable conductor 272 and a coil electrode 230. FIG. 4 illustrates an exploded view of the coupling 200. The coupling 200 can include an inner fitting 280 and an outer tubular fitting 282. The inner fitting 280 can be a tubular body. The inner fitting 280 can have a lumen 260 that extends the full length of the inner fitting 280. The inner fitting 280 can have a first portion 224 and a second portion 226. External threading 240 can extend along the first portion 224. The second portion 226 can be a longitudinal section of the inner fitting 280 that has no external threading. A hole 228 and/or other attachment feature for facilitating a connection to polymer material can be provided along the second portion 226. The inner fitting 280 may be formed from metal, such as platinum or titanium. The inner fitting 280 can be formed by, for example, one or more of casting, extrusion, stamping, and/or machining processes.

The inner fitting 280 can include a connector 250. As shown in FIG. 4, the connector 250 can be within the lumen 260 and along the second portion 226. In some other embodiments the connector 250 can be located along the first portion 224 or other location. The connector 250 can connect to the cable conductor 272 as described herein (e.g., by crimping the connector 250 over the cable conductor 272).

The outer tubular fitting 282 can define an exterior surface of the implantable lead 106. The outer tubular fitting 282 can have a lumen 264. The lumen 264 can extend through the outer tubular fitting 282 to have openings on each side of the outer tubular fitting 282. The outer tubular fitting 282 and the inner fitting 280 can be dimensioned such that the inner fitting 280 can be received within the lumen 264 of the outer tubular fitting 282. The outer tubular fitting 282 may be formed from metal, such as platinum or titanium. The outer tubular fitting 282 can be formed by one or more of casting, extrusion, stamping, and/or machining processes.

The lumen 264 of the outer tubular fitting 282 can include internal threading 262. The internal threading 262 can be formed by one or more spiraling features projecting inward from an inner surface of the lumen 264. The internal threading 262 can have a pitch. The internal threading 262 can have the same pitch as the external threading 240 of the inner fitting 280. The internal threading 262 can be complementary to the external threading 240 such that the internal threads 262 can receive the external threads 240 by rotation. Engagement between the internal threading 262 and the external threading 240 can mechanically connect the inner fitting 280 to the outer tubular fitting 282. The inner fitting 280 can additionally or alternatively be mechanically connected to the outer tubular fitting 282 by welding. For example, the outer tubular fitting 282 can include a window 234. The window 234 can allow welding of the inner fitting 280 to the outer tubular fitting 282 within the lumen 264 when the inner fitting 280 is received within the lumen 264.

FIG. 4 further illustrates an end of the coil electrode 230. The coil electrode 230 can be similar to the coil electrode 130 of FIGS. 1-3B. The coil electrode 230 can have filars 244-246 wound in a helical pattern, the helical pattern having a pitch. The pitch of the filars 244-246 can be similar to the pitch of the external threading 240 and the internal threading 262. The helical pattern of the filars 244-246 can form a helical contour pattern along the exterior of the coil electrode 230. The helical contour pattern can be complementary to the internal threading 262 of the lumen 264 of the outer tubular fitting 282. For example, an end (e.g., a proximal end) of the coil electrode 230 can be rotateably advanced into the lumen 264 to interlock the filars 244-246 and the internal threading 262 as the end of the coil electrode 230 is received within the lumen 264.

The outer diameter of the coil electrode 230 can be about the same as the outer diameter of the first portion 224 of the inner fitting 280. Similarity between the outer diameters of the coil electrode 230 and the inner fitting 280 as well as correspondence between the pitches of the helical contour pattern of the coil electrode 230 and the external threading 240 of the inner fitting 280 can allow the coil electrode 230 and the inner fitting 280 to form a continuous thread pattern that extends over each of the coil electrode 230 and the inner fitting 280 when axially aligned. For example, each of the coil electrode 230 and the inner fitting 280 can be at least partially received within the lumen 264 of the outer tubular fitting 282 at the same time. Furthermore, both of the external threading 240 of the inner fitting 280 and the helical pattern of the filars 244-246 can engage with the internal threading 262 of the outer tubular fitting 282 at the same time.

In some embodiments, the coil electrode 230 can be mechanically attached to the inner fitting 280 prior to being received within the lumen 264 of the outer tubular fitting 282. For example, an end of the coil electrode 230 (e.g., a proximal end) can be brought into contact with an end of the inner fitting 280 (e.g., a distal end) while the coil electrode 230 and the inner fitting 280 are in axial alignment. The coil electrode 230 can then be welded to the inner fitting 280. The welding can provide an electrical connection between the coil electrode 230 and the inner fitting 280. Alternative techniques for mechanically coupling the coil electrode 230 and the inner fitting 280 can be performed. After the coil electrode 230 is mechanically connected to the inner fitting 280, the assembly of the coil electrode 230 and the inner fitting 280 can be moved through the lumen 264 by rotation until the internal threading 262 engages both of the external threading 240 and the filars 244-246.

FIG. 5 shows a cross sectional diagram of the coupling 200 in an assembled configuration. As shown in FIG. 5, the coil electrode 230 and the inner fitting 280 can be received within the outer tubular fitting 282 such that the outer tubular fitting 282 can overlap at least part of each of the coil electrode 230 and the inner fitting 280. FIG. 5 further shows that the internal threading 262 can threadedly engage with each of the external threading 240 of the inner fitting 280 and the helical contour pattern of the coil electrode 230. The cable conductor 272 may not be in direct contact with the coil electrode 230 in the embodiment of FIG. 5, however each of the cable conductor 272 and the coil electrode 230 can be in contact with one or both of the inner fitting 280 and the outer tubular fitting 282 in various other embodiments to conduct electrical energy from the cable conductor 272 to the coil electrode 230.

FIG. 5 further illustrates a polymer sleeve 270. The polymer sleeve 270 can be similar to the polymer sleeve 170 discussed herein. For example, the polymer sleeve 270 can be secured to the outer tubular fitting 282 by being pinched between an inner surface of the outer tubular fitting 282 (e.g., the internal threading 262) and the filars 244-246.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An implantable lead comprising:
a lead body having a proximal end and a distal end;
a conductor extending within the lead body;
a coil electrode having a proximal end, a distal end, and one or more filars, the coil electrode extending along a portion of the distal end of the lead body and configured to deliver defibrillation therapy to tissue, the one or more filars wound in a helical pattern to have a pitch;
a tubular fitting having a lumen, the tubular fitting formed from an electrically conductive metal, at least a portion of the lumen having threading that corresponds to the pitch of the one or more filars, the tubular fitting electrically connecting the conductor to the coil electrode, wherein the tubular fitting comprises:
an inner fitting axially aligned with the coil electrode, at least a portion of the inner fitting comprising external threading; and
an outer tubular fitting, the outer tubular fitting defining the lumen, the inner fitting at least partially received within the lumen, both of the external threading and the one or more filars threadedly engaged with the threading of the lumen; and
a polymer sleeve having a wall, the polymer sleeve extending over the coil electrode, the wall of the polymer sleeve configured to allow the delivery of the defibrillation therapy through the wall,
wherein one of the proximal end or the distal end of the coil electrode is within the lumen of the tubular fitting and the coil electrode is mechanically connected to the tubular fitting by interaction between the threading of the lumen and the one or more filars, and wherein the polymer sleeve extends into the lumen of the tubular fitting, and the wall of the polymer sleeve is pinched between the threading of the lumen and the one or more filars to mechanically couple the polymer sleeve to the tubular fitting.

2. The implantable lead of claim 1, wherein the polymer sleeve is made of expanded polytetrafluoroethylene (ePTFE).

3. The implantable lead of claim 1, wherein the one or more filars comprises a plurality of filars arranged in a grouping of adjacent filars that spirals in the helical pattern, and a space exists between each turn of the grouping.

4. The implantable lead of claim 3, wherein the threading is dimensioned such that each thread projects into the space between each turn of the grouping.

5. The implantable lead of claim 1, wherein the tubular fitting comprises at least one window that allows welding between the coil electrode and the tubular fitting.

6. The implantable lead of claim 1, wherein the tubular fitting further comprises a stop within the lumen, the stop limiting the extent to which the proximal end or the distal end of the coil electrode can extend into the lumen.

7. The implantable lead of claim 6, wherein the coil electrode is in contact with the stop, and the contact between the coil electrode and the stop provides an electrical connection between the tubular fitting and the coil electrode.

8. The implantable lead of claim 1, wherein the tubular fitting further comprises a connector within the lumen, and the conductor is mechanically and electrically connected to the connector.

9. The implantable lead of claim 8, wherein the conductor is a cable conductor and the connector is a crimp connector that is crimped over the cable conductor.

10. The implantable lead of claim 1, wherein the tubular fitting defines at least part of an exterior surface of the implantable lead.

11. An implantable lead comprising:
a lead body having a proximal end and a distal end;
a conductor extending within the lead body;
a coil electrode having a proximal end, a distal end, and one or more filars, the coil electrode extending along a portion of the distal end of the lead body and configured to deliver defibrillation therapy to tissue, the one or more filars wound in a helical pattern to have a pitch; and a tubular fitting having a lumen, the tubular fitting formed from an electrically conductive metal, at least a portion of the lumen having threading that corresponds to the pitch of the one or more filars, the tubular fitting electrically connecting the conductor to the coil electrode, wherein the tubular fitting comprises:

an inner fitting axially aligned with the coil electrode, at least a portion of the inner fitting comprising external threading; and an outer tubular fitting, the outer tubular fitting defining the lumen, the inner fitting at least partially received within the lumen, both of the external threading and the one or more filars threadedly engaged with the threading of the lumen;

wherein one of the proximal end or the distal end of the coil electrode is within the lumen of the tubular fitting and the coil electrode is mechanically connected to the tubular fitting by interaction between the threading of the lumen and the one or more filars.

12. The implantable lead of claim 11, further comprising a polymer sleeve having a wall, the polymer sleeve extending over the coil electrode, the wall of the polymer sleeve configured to allow the delivery of the defibrillation therapy through the wall.

13. The implantable lead of claim 12, wherein the polymer sleeve extends into the lumen of the tubular fitting, and the wall of the polymer sleeve is pinched between the threading of the lumen and the one or more filars to mechanically couple the polymer sleeve to the tubular fitting.

14. The implantable lead of claim 12, wherein the polymer sleeve is made of expanded polytetrafluoroethylene (ePTFE).

15. The implantable lead of claim 11, wherein the one or more filars comprises a plurality of filars arranged in a grouping of adjacent filars that spirals in the helical pattern, and a space exists between each turn of the grouping.

16. The implantable lead of claim 11, wherein the tubular fitting comprises at least one window that allows welding between the coil electrode and the tubular fitting.

17. The implantable lead of claim 11, wherein the tubular fitting further comprises a stop within the lumen, the stop limiting the extent to which the proximal end or the distal end of the coil electrode can extend into the lumen.

18. The implantable lead of claim 11, wherein the tubular fitting further comprises a connector within the lumen, and the conductor is mechanically and electrically connected to the connector.

19. The implantable lead of claim 18, wherein the conductor is a cable conductor and the connector is a crimp connector that is crimped over the cable conductor.

20. The implantable lead of claim 11, wherein the tubular fitting defines at least part of an exterior surface of the implantable lead.

* * * * *